United States Patent [19]

Brun et al.

[11] Patent Number: 5,597,721

[45] Date of Patent: Jan. 28, 1997

[54] PREPARATION OF ANTIGENS OF AND OF VACCINES FOR THE VIRUS OF MYSTERY DISEASE, ANTIGENS AND VACCINES OBTAINED FOR THE PREVENTION OF THIS DISEASE

[75] Inventors: André Brun, Caluire; Marie-Claude Tardy, Lyons; Alain Vaganay, Villeurbanne; Joris Vandeputte, Diemoz, all of France

[73] Assignee: Rhone Merieux, Lyons, France

[21] Appl. No.: 256,539

[22] PCT Filed: Jan. 13, 1993

[86] PCT No.: PCT/FR93/00026

§ 371 Date: Sep. 21, 1994

§ 102(e) Date: Sep. 21, 1994

[87] PCT Pub. No.: WO93/14196

PCT Pub. Date: Jul. 22, 1993

[30] Foreign Application Priority Data

Jan. 14, 1992 [FR] France ........................... 92 00294

[51] Int. Cl.⁶ .................. C12N 7/00; A61K 39/145; A61K 39/155; A61K 39/295
[52] U.S. Cl. .................. 435/235.1; 424/202.1; 424/209.1; 424/211.1; 424/218.1
[58] Field of Search ................ 424/209.1, 211.1, 424/202.1, 218.1; 435/235.1, 236, 237, 238, 239

[56] References Cited

U.S. PATENT DOCUMENTS 4,070,453  1/1978  Bordt et al. .................. 435/240.21
5,476,778  12/1995  Chladek et al. .................. 435/235.1

FOREIGN PATENT DOCUMENTS 145705     1/1981   German Dem. Rep. .
50-052224  5/1975   Japan .
58-079929  5/1983   Japan .
59-02847   8/1984   Japan .
62-198626  9/1987   Japan .
16-04851   11/1990  U.S.S.R. .

OTHER PUBLICATIONS

Wensvoort et al., The Veterinary Quarterly, vol. 13 (No. 3), pp. 121–130, (1991).
Terpstra et al., The Veterinary Quarterly, vol. 13 (No. 3), pp. 131–136, (1991).
Abstract, "Dutch Team Isolates Mystery Pig Disease Agent", Jun. 21, 1991, Animal–Pharm, vol. 230, p. 21 (no author listed).
Baron et al , "Report on the first outbreaks of the porcine . . . ", Ann. Rech. Vet., 1992, vol. 23, pp. 161–166.
Benfield et al, "Characterization of swine infertility . . . ", J. Vet. Diagn. Invest., vol. 4, pp. 127–133, 1992.
Albina et al, "An enzyme linked immunosorbent assay (ELISA) . . . ", Ann. Rech. Vet. vol. 23, pp. 167–176, 1992.
Bonn Symposium Abstract, "Fresh clues to mystery pig disease . . . ", Animal–Pharm, vol. 228, p. 3.

*Primary Examiner*—Mindy Fleisher
*Assistant Examiner*—Terry A. McKelvey
*Attorney, Agent, or Firm*—Larson & Taylor

[57] ABSTRACT

Two joint agents responsible for the disease called Mystery Disease have been isolated. Compositions comprising purified viral particles of Mystery Disease virus (A) and/or purified viral particles of Mystery Disease virus (B), and an appropriate vehicle have been described.

3 Claims, 1 Drawing Sheet

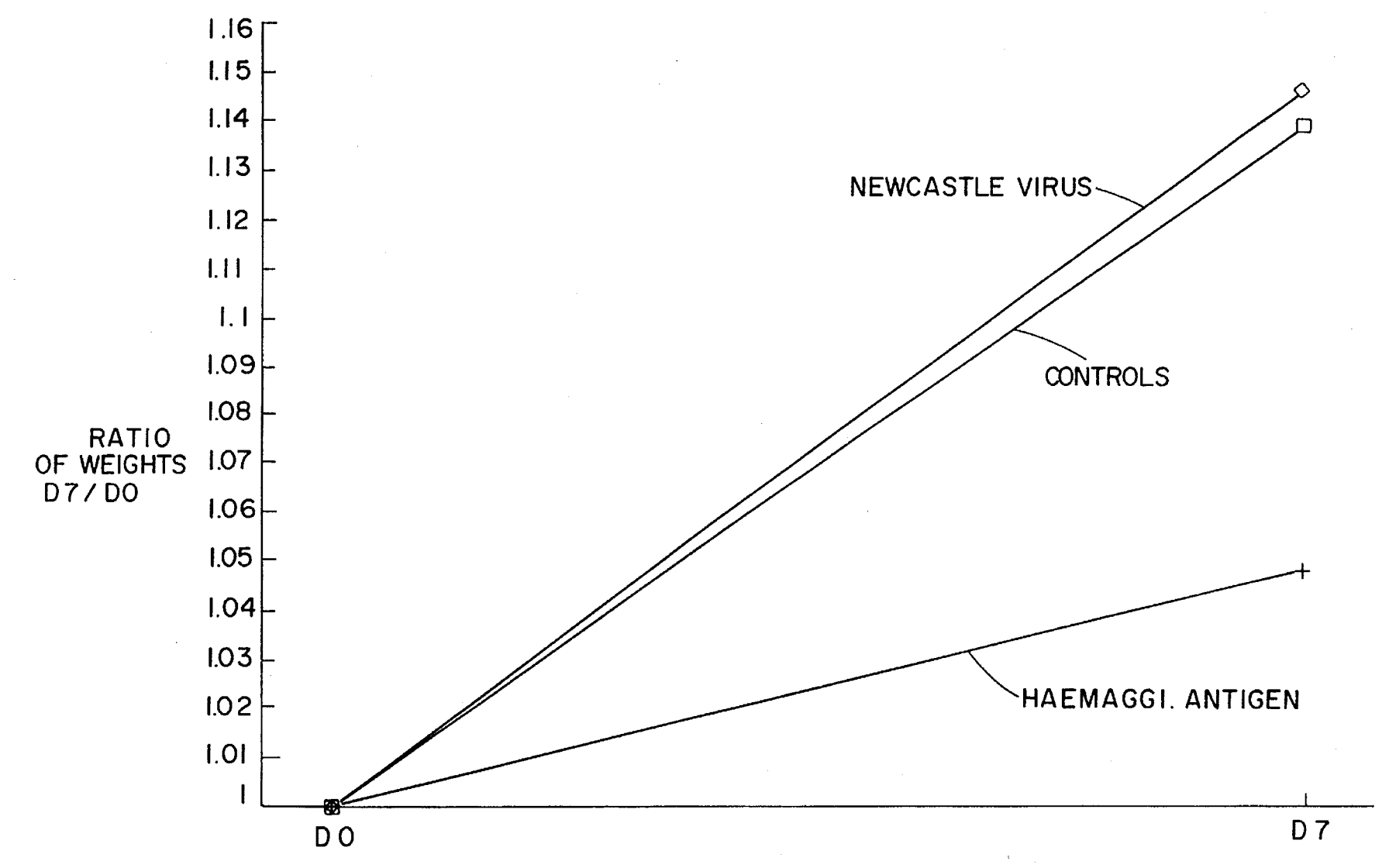

PREPARATION OF ANTIGENS OF AND OF VACCINES FOR THE VIRUS OF MYSTERY DISEASE, ANTIGENS AND VACCINES OBTAINED FOR THE PREVENTION OF THIS DISEASE

CROSS-REFERENCES TO RELATED APPLICATIONS

This application is a US national stage application of PCT/FR93/00026 filed Jan. 13, 1993 and published as WO93/14196 Jul. 22, 1993.

BACKGROUND OF THE INVENTION

The present invention relates to the preparation of antigens of and of vaccines for the virus of Mystery Disease, as well as to the antigens and to the vaccines obtained.

The disease called Mystery Disease (M.D.) or also Porcine Reproductive Respiratory Syndrome (P.R.R.S.) began to acquire an identity of its own in pigs, in 1986 in the United States and in 1990 in Europe. This disease manifests itself essentially in pigs by signs of exhaustion, anorexia and hyperthermia of the order of 40° C., which are conventionally observed in sows in pig farms affected by the disease. These signs are accompanied or followed by reproductive disorders (premature or late farrowing and birth of stillborn, mummified or sickly piglets, and return of the sows to heat). A respiratory syndrome can be observed in piglets with interstitial pneumonia lesions. Older pigs can also be affected by respiratory disorders. All this symptomatology can be accompanied by diseases caused by chance infections conventionally observed in pigs.

In G. Wensvoort et al., Mystery Swine Disease in the Netherlands: the isolation of Lelystad virus, The Veterinary Quarterly, Vol. 13, No. 3, 19 Jul. 1991, the isolation of an agent associated with the disease called Mystery Disease is described, which is characterized as a virus, designated Lelystad virus, and which is presented as the causative agent of the disease. This discovery might constitute a first step for the search for a vaccine against this disease.

A process for the industrial production of this virus or of antigen of this virus was not available, the culture seeming possible only in pig alveolar macrophages.

SUMMARY OF THE INVENTION

Yet, the inventors have succeeded in isolating and in identifying another virus, responsible for this disease. This virus is the Myxovirus type, according to the analysis carried out in the electron microscope, and has the characteristic of not being neutralized by porcine anti-influenza sera H1N1 and H3N2.

A strain of this virus identified under the name P129-294 was deposited in the Collection Nationale de Cultures de Micro-organismes held at the Institut Pasteur under No. I-1153.

In French Patent Application No. 91 13338 filed on 29 Oct. 1991, the inventors described a process for isolating the virus and its use for the preparation of antigens, a process for the industrial production of this virus, as well as the vaccines produced from the above-mentioned antigens containing an effective vaccinating quantity of antigens, in suitable vehicles.

Yet, parallel to the discovery and use of this other virus, of which a strain has been deposited on Oct. 11, 1991 in the Collection Nationale de Cultures de Microorganismes Instit Pasteur, 25, Rue du Docteur Roux, 75724 Paris Cedex 15, FRANCE under the name P129-294 deposit No. I-7153, they also isolated from the same sow obtained from a German pig farm and identified under the No. 294, a completely different virus, including a strain identified under the name P129-294B. They also isolated another viral strain from organs from a piglet from a German farm, collected on 13 Feb. 1991, this strain being identified under the name P120-117B.

The inventors were able to establish that both viruses, namely the Myxovirus-type virus (for example P129-294), designated below A virus, and the viruses corresponding to the strain P120-117B, called hereinafter B virus, occur associated in the samples collected from sick or infected pigs and in the same organs, and can be considered as joint agents responsible for the disease called Mystery Disease.

The subject of the present invention is therefore a process for isolating the B viruses and its use for the preparation of antigens.

A process isolating a B virus can comprise the passage through pig lung or peritoneal macrophages.

In an improved embodiment of the invention, the isolation of the B virus can be combined with the isolation of the A virus in the same isolation process. Isolation processes comprise the taking of samples of organs of sick or infected animals, or of blood, passages of supernatants of milled organs or of blood constituents through sensitive heterologous or homologous cells, such as especially pig primary cells, cells of the porcine or heterologous line, such as cells of the Vero, MDCK (in the presence of trypsin), ST and BHK line.

The samples are preferably taken from the lung of the infected animal or else from a pool of organs comprising, for example, heart, spleen, liver, kidney and lymphoid tissues.

The viral harvests do not haemagglutinate chicken red blood cells, are sensitive to chloroform, react with convalescent sera obtained from infected farms as demonstrated by indirect immunofluorescence. The structure under an electron microscope demonstrates enveloped structures of a size of about 50 nm.

The subject of the invention is also a process for the industrial production of the B virus and, preferably, simultaneously of the A virus, on sensitive heterologous or homologous cells, such as cells of the Vero, MDCK, ST or BHK line, primary macrophages or lines, primary cells or cell line of pulmonary or embryonic origin. The virus can be used for the preparation of antigens.

The process for the industrial production of the A virus, described in the aforementioned French Patent Application, had remarkably simultaneously produced the B virus.

The virus, or the mixture of virus, harvested can be used for the preparation of antigens. To this end, it is preferably suitably purified according to the usual procedures, for example ultracentrifugation or chromatography. It can also be concentrated by the usual techniques.

According to the envisaged use, the antigen preparations according to the invention may consist of live viral particles, attenuated or not, of inactivated particles, of subunit antigens or else antigens obtained by genetic recombination from genes or isolated viruses, inserted so as to be expressed in the genome procaryotic or eucaryotic recombinant hosts.

The subject of the invention is also the vaccines produced from at least one of the abovementioned antigens, containing an effective vaccinating quantity of antigens, in suitable vehicles.

Preferably, the vaccines according to the invention contain the antigens of the A virus, in combination with B virus antigens, and optionally other infectious antigens for the immunization of pigs or other animal species.

These vaccines may be intended to be administered to pigs but also to other animals which may prove sensitive to this virus.

An attenuated vaccine can be prepared by passage of the virus through a cell culture.

The quantity of each virus per vaccinal dose is preferably between $10^3$ and $10^8$ $DICC_{50}$ per dose.

The live attenuated vaccine may be provided in liquid or freeze-dried form in the presence of a wide variety of formulation stabilizers which may include sugars, proteins and buffers. The vaccine can be supplemented with inorganic or organic adjuvents.

The live vaccine can be administered to animals to protect them from the beginning of the fattening period or before artificial insemination or covering, or during gestation, in one and preferably in two injections at three or four weeks' interval.

An inactivated vaccine can be prepared from vital suspensions obtained by passages through homologous (porcine) or heterologous cellular systems followed by inactivation by the usual chemical inactivating agents such as beta-propiolactone, enzymes or organic solvents or detergents. The inactivation can also be obtained by physical action such as ultraviolet radiation, gamma irradiations or X-rays. The inactivating agent can be neutralized if necessary.

The inactivated vaccine preferably contains at least the equivalent of $10^5$ $DICC_{50}$ of each virus per vaccinal dose, a concentration which is determined before inactivation.

The inactivated vaccine can be administered to animals to protect them from the beginning of the fattening period, or before artificial insemination or covering, or during gestation, in one or preferably two injections at three or four weeks' interval. It is preferred that the vaccine contains an adjuvant of inorganic or organic origin.

A recombinant vaccine can be obtained for example by inserting the sequence encoding the desired antigen of the virus into the genome of the host. The host can be a virus, especially for the preparation of a live vaccine.

This host can also be a bacterial system, a yeast system or a system of other eucaryotic cells. In this case, the host is preferably used for the production of antigens which are then purified and conditioned in order to make the vaccine.

The vaccine can be provided in monovalent form or associated with other viral or bacterial agents responsible for diseases in pigs.

The subject of the invention is also antigen preparations for diagnostic purposes, characterized in that they contain A virus antigens or a mixture of A and B virus antigens. These antigen preparations for diagnostic purposes are prepared in the usual manner and comprise the usual means permitting the identification and optionally the quantification of positive serological reactions.

The subject of the invention is also the preparations of antibodies against these antigens, which can be used for diagnosis of the disease.

Other advantages and characteristics of the invention will become apparent on reading the following description, given by way of non-limiting example.

BRIEF DESCRIPTION OF THE DRAWING

FIG. 1 consists of a graph plotting the weights at day 7 divided by the weights at day 0 of SPF pigs treated with a viral suspension of P129-294 (+), SPF pigs treated with Newcastle virus (diamond), and control SPF pigs treated with undiluted allantoidian liquid (square), versus days after treatment.

DESCRIPTION OF THE PREFERRED EMBODIMENTS

Example 1: Isolation of the P129-294 Virus
Example A:
Tests on chick embryos
 Inoculation in SPF chick embryos of 9 days
 Inoculum: SL of milled lung preparation from the sow 294. 0.1 ml of undiluted inoculum or inoculum diluted to $\frac{1}{10}$ in PBS+antibiotics is inoculated intra-allantoidally.

After incubating for 3 days, the eggs are emptied and the allantoic liquid is harvested (individual harvesting from each egg).

A hemagglutination test with respect to chicken red cells (concentration $20.10^6$ red cells per ml) is carried out on all the harvested samples.
successive passages are carried out.
Results in eggs
 First passage: no hemagglutination could be shown.
 Second passage: 1 egg shows hemagglutination. The hemagglutination titre HA is 640.
 Third passage:
 HA titre which can reach 1024.
 presence of HA not neutralized by porcine anti-influenza sera H1N1 of H3N2.
 Fourth passage: hemagglutination confirmed with titres which can reach 2048.

Additionally, a significant mortality in the eggs could be observed in the second, third and fourth passages, it being possible for the mortality to exceed 50% of the inoculated eggs.

A positive hemagglutination test was carried out with respect to guinea pig red cells. Using the hemagglutinating antigen of the 3rd passage, cells of ST and Vero lines of primary pig kidney cells SPF were inoculated, a cytopathegenic effect was observed in these 3 cells, a cytopathogenic effect more marked than in the cells inoculated directly with lung SL. The hemagglutinating effect had disappeared after passages through cells.

From the viral suspension of the 3rd passage through eggs, 2 pigs with a weight of 30 kg were inoculated intravenously with a volume of 1 cc. These 2 pigs showed signs of exhaustion, anorexia and hyperthermia of the order of 40° C. for at most 7 days. These symptoms are commonly observed in sows in pig farms attacked by P.R.R.S. or M.D.

Example 2: Isolation of the P120-117B Virus from the organs of a piglet collected on 13 Feb. 1991.
a) Method:
Milled preparations of organs: the organ is milled in MEM medium plus antibiotics.
Dilution: weight of the organ per volume of about 1 to 10.
Clarifying centrifugation for recovery of the supernatant liquid (SL).
Filtration at 0.22μ.
b) Tests on cell cultures:
First passages: the SL is inoculated into an established cell layer of SPF pig lung macrophages. Three days after inoculation, cytopathogenic effect was observed which manifests itself by a morphological modification of the macrophages, at various stages of development. This cytophathogenic effect is maximum on the fifth day.

Example 3: Serological study

The antigens consisting of P120/177 B viral preparations, as well as of two other viral strains P206 and P208 were tested with respect to:

a customary reference serum, called Ploufragan;

sera from sows having served for the experimental reproduction of the disease (samples taken 21 days after inoculation and after farrowing of sows);

sera from piglets experimentally inoculated intranasally.

This serological evaluation by indirect immunofluorescence reaction is the following:

|  | P120/117 B | P206 or P208 |
| --- | --- | --- |
| Ploufragan sera | + | + |
| Sow sera | − | − |
| Piglet sera | + | + |

The viral strain P129-294: the vital agent isolated on eggs was inoculated in the form of a viral suspension of allantoidian liquid from the third passage, into 2 SPF pigs, intravenously in a volume of 1 cm$^3$. 2 other SPF pigs were also intravenously inoculated with Newcastle virus, Texas strain. 2 pigs were kept as controls and inoculated with non-diluted allantoidian liquid. The animals were stabled in different boxes. They were observed for 14 days with daily measurement of temperature and weighing on days 0 and 7. Blood samples were taken on days 0 and 14.

The 2 pigs inoculated with the haemagglutinating agent had a hyperthermia of between 39°5 and 40° C. between day 1 after inoculation and day 7, whereas the other 4 pigs never had this rise in temperature. Traces of vomit were noted on day 2 in the box of the 2 pigs inoculated with the haemagglutinating agent. Moreover, a few days' inappetence was observed in these 2 animals, which manifests itself by a very clearly unfavourable weight variation for these 2 animals compared with those inoculated either with the control allantoidian liquid or with the Newcastle virus. The graph (FIG. 1) illustrates this difference in growth. Upon autopsy, one of the 2 pigs inoculated with the haemagglutinating agent had slightly marked pneumonia lesions.

Conclusion: the P129-294 virus is responsible for clinical signs in the piglets, appearing in the form of hyperthermia and anorexia. This clinical combination reproduces the observations made on the infected farms. Finally, this virus was isolated from the same organ, the lung, from the same sow.

Example 5: Study of the pathogenicity of the 120/117 B Virus.

An experimental inoculation performed on piglets with a weight of about 20 kg, by means of the strain P120/117 B, administered intranasally with an inoculum titrating $10^{5.5}$ DICC$_{50}$/ml results in a fever and inappetence for a few days.

Example 6: Serological monitoring. Presence of antibodies against the P129-294 strain.

238 sera obtained from infected farms were examined for the presence of antibodies against the P129-294 strain.

On these farms, clear signs of Mysterious Disease of pigs were observed (abortions, respiratory problems). The serological method is an indirect Elisa tests the antigen used is an antigen obtained on eggs after ultracentrifugation. The sera to be tested are treated beforehand by means of a negative egg antigen having undergone the same ultracentrifugation treatment. The 238 sera obtained from infected farms in Germany, Belgium and Holland have highly positive antibodies for 43% of them, weakly positive for 37% and negative for 20%.

Conclusion: In the clinical cases of Mysterious Disease, a positive serology is observed against the P129-294 strain in 80% of cases. It should be noted that sera obtained from non-suspect farms are negative, or that the frequency of positivity is significantly lower than that observed on clinically affected farms.

These results show the importance of Myxovirus A infection in the Mysterious Disease syndrome.

Example 7: Preparation of live vaccine.

The P129-294 and P120-117B or P129-294B viruses are multiplied by passages through one or more adapted cell systems. The harvest is treated depending on the vaccine which is produced: freeze-dried vaccine for taking up in aqueous solvent, in oily solvent or in other vaccines. It can also be provided in liquid vaccine in aqueous or oily solvent or in another vaccine.

Example 8: Production of inactivated vaccine.

The P129-294 and P120-117B viruses are multiplied on BHK or Vero cells or macrophages or porcine cell line, and inactivated with beta-propiolactone, ethylene-imine, and then supplemented with an aqueous or oily adjuvant.

The P120-117B has been deposited in the Collection Nationale de Cultures de Microorganisms, Instit Pasteur, 25, Rue du Docteur Roux, 75724 Paris Cedex 15, France (CNCM):

P120-117B was deposited (Jan. 14, 1992) under No. I-1163

The P120-117B virus appears as a togavirus.

We claim:

1. A composition comprising purified viral particles of Mystery Disease virus (A) deposited in the CNCM under deposit no. I-1153 and a carrier.

2. A composition comprising purified viral particles of Mystery Disease virus (A) deposited in the CNCM under deposit no. I-1153, purified viral particles of Mystery Disease virus (B) deposited in the CNCM under deposit no. I-1163, and a carrier.

3. A composition comprising purified viral particles of Mystery Disease virus (B) deposited in the CNCM under deposit no. I-1163 and a carrier.

* * * * *